United States Patent
Sayeed

(10) Patent No.: US 10,434,338 B2
(45) Date of Patent: Oct. 8, 2019

(54) DOSIMETRY TECHNIQUES FOR RADIOTHERAPY

(71) Applicant: Elekta Limited, West Sussex (GB)

(72) Inventor: Abdul Sayeed, Surrey (GB)

(73) Assignee: ELEKTA LIMITED, West Sussex (GB)

( * ) Notice: Subject to any disclaimer, the term of this patent is extended or adjusted under 35 U.S.C. 154(b) by 446 days.

(21) Appl. No.: 15/179,467

(22) Filed: Jun. 10, 2016

(65) Prior Publication Data

US 2016/0361570 A1    Dec. 15, 2016

(30) Foreign Application Priority Data

Jun. 12, 2015 (GB) .................................. 1510292.4

(51) Int. Cl.
    *A61N 5/10*      (2006.01)

(52) U.S. Cl.
    CPC .......... *A61N 5/1071* (2013.01); *A61N 5/1031* (2013.01); *A61N 5/1039* (2013.01); *A61N 5/1064* (2013.01); *A61N 5/1077* (2013.01)

(58) Field of Classification Search
    CPC ........ A61N 5/1071; A61N 5/103–1084; A61N 2005/1072; A61N 2005/1076
    See application file for complete search history.

(56) References Cited

U.S. PATENT DOCUMENTS

| | | | |
|---|---|---|---|
| 2007/0071169 A1 | 3/2007 | Yeo et al. | |
| 2010/0012829 A1* | 1/2010 | Islam | A61N 5/1048 250/252.1 |
| 2013/0114784 A1* | 5/2013 | Nioutsikou | A61N 5/1038 378/4 |
| 2014/0105355 A1 | 4/2014 | Toimela et al. | |
| 2014/0336438 A1* | 11/2014 | Bharat | A61N 5/1031 600/1 |
| 2015/0095043 A1 | 4/2015 | Cordero Marcos et al. | |
| 2015/0124930 A1 | 5/2015 | Verhaegen et al. | |
| 2016/0287906 A1* | 10/2016 | Nord | A61N 5/103 |

FOREIGN PATENT DOCUMENTS

| | | |
|---|---|---|
| EP | 2904974 A1 | 9/2015 |
| WO | WO 2008/013598 A1 | 1/2008 |
| WO | WO 2013/080175 A1 | 6/2013 |

OTHER PUBLICATIONS

International Search Report for related GB Application No. 1510292.4, filed Jun. 12. 2015 (dated Dec. 15, 2015).

(Continued)

*Primary Examiner* — Thaddeus B Cox

(74) *Attorney, Agent, or Firm* — Finnegan, Henderson, Farabow, Garrett & Dunner LLP

(57) ABSTRACT

Embodiments of the present disclosure provide improved techniques for dosimetry in radiotherapy treatment. In a fractionated radiotherapy treatment, the expected dose buildup is computed in advance of a fraction delivery based on the instructions in the treatment plan. The progress of the fraction is then monitored using an electronic portal image detector (EPID), and fluence data from the EPID used to calculate an estimate of the actual dose build-up in real time. This estimate can be compared to the expected dose buildup in order to validate the fraction.

17 Claims, 2 Drawing Sheets

(56) References Cited

OTHER PUBLICATIONS

International Search Report for related GB Application No. 1510238.2, filed Jun. 12, 2015 (dated Dec. 15, 2015).

Van Elmpt et al. "3D dose delivery verification using cone-beam imaging and EPID dosimetry for sterotactic body radiotherapy of non-small cell lung cancer." Radiotherapy and Oncology 94 (2010): 188-194.

Van Elmpt et al. "3D in Vivo Dosimetry using Megavoltage Cone-Beam CT and EPID Dosimetry." International Journal of Radiation Oncology, Biology, Physics vol. 73, No. 5 (2009): 1580-1587.

* cited by examiner

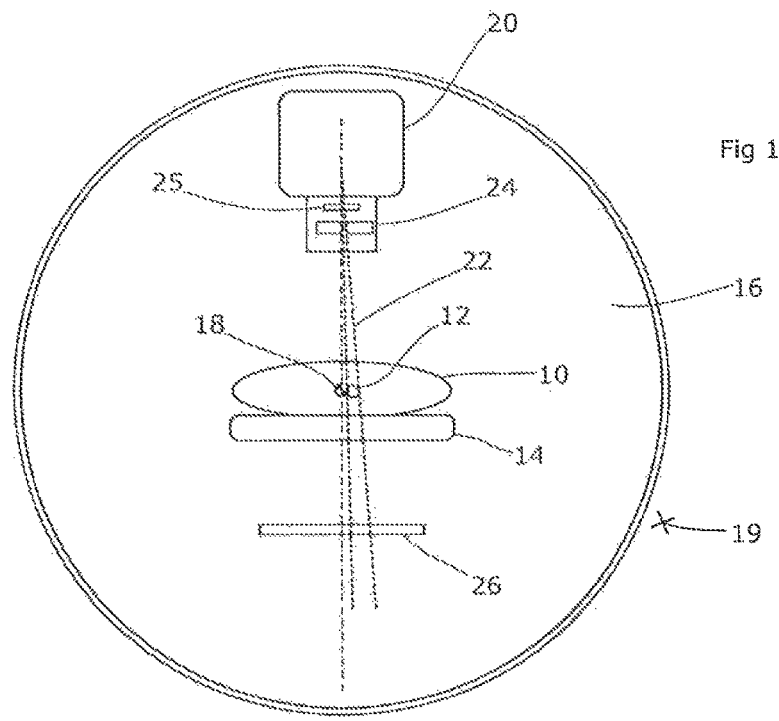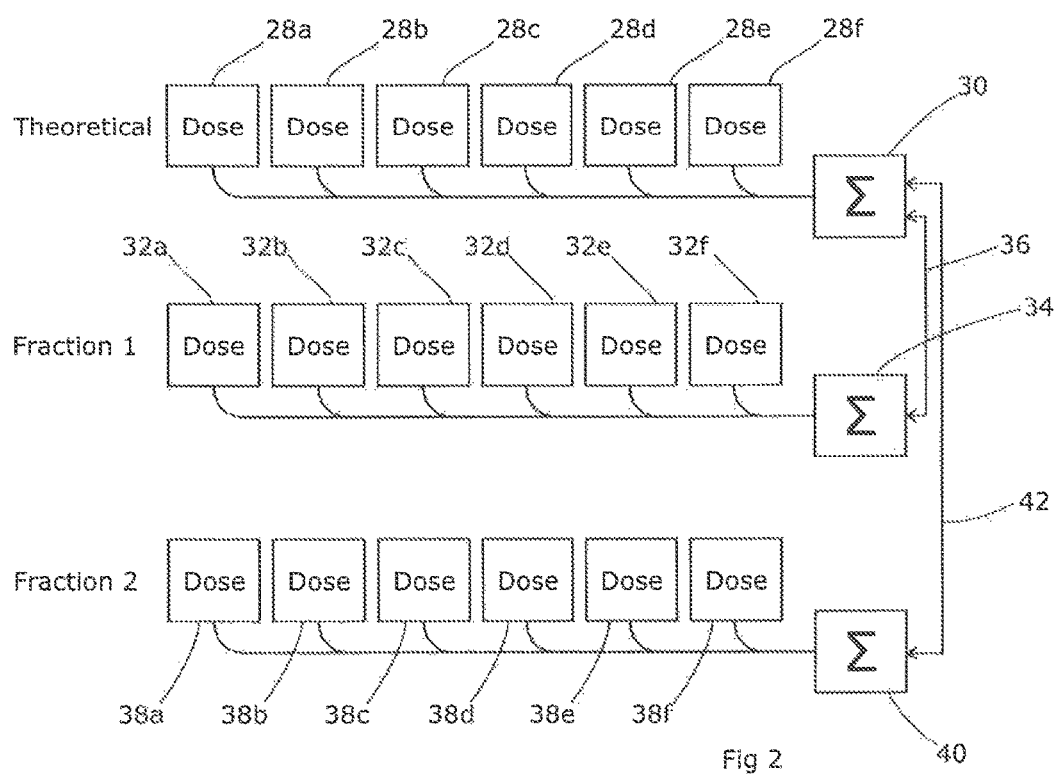

DOSIMETRY TECHNIQUES FOR RADIOTHERAPY

CROSS-REFERENCE TO RELATED APPLICATION

This application claims the benefit and priority of prior United Kingdom Patent Application No. 1510292.4, filed on Jun. 12, 2015, the entire contents of which are incorporated by reference herein.

FIELD OF THE INVENTION

The present invention seeks to improve upon existing techniques for dosimetry in radiotherapy treatment. It aims to move towards providing a form of real-time in-vivo dosimetry.

BACKGROUND ART

Radiotherapy apparatus delivers a beam of high-energy radiation (typically in the MeV range, apt to damage tumour cells) which is directed towards a tumour site (or other lesion) in a collimated and controlled manner. Thus, the lateral extent of the beam is limited by collimating elements so as to match a pattern determined in a predetermined treatment plan, such as the external profile of the tumour or a subsection of it. The direction of the beam is also varied, so that the tumour is irradiated from multiple directions, thereby reducing the dose delivered to tissue surrounding the tumour site. The treatment is also delivered in "fractions", i.e. individual fractional doses delivered at intervals of (for example) a day, which add up to a total dose to be delivered; delivering the dose in fractions alleviates the side-effects on the healthy tissue surrounding the tumour site.

Typically, a treatment plan will be drawn up prior to delivery of the first fraction, which will detail the beam shapes, directions, and intensity/duration of a number of beam segments that together will form the first fraction. These beam segments are designed to, collectively, deposit a three-dimensional dose distribution in the tumour which corresponds to that prescribed by a clinician, and which both generally minimises the dose delivered to non-tumour areas, and remains within upper dose limits for certain designated sensitive areas of the patient. This is a challenging problem, and the treatment plan is generally arrived at by an iterative process carried out on a computational device.

It is now fairly common for radiotherapy apparatus to have a detector, usually attached to the gantry, located opposite the high-energy radiation source and positioned so as to detect the radiation beam after it has passed through the patient. Such "portal imagers" usually comprise a flat-panel detector (in the form of an electronic portal image detector, or "EPID") which can create an image of the treatment beam as attenuated by the patient: from this image and from a priori knowledge of the beam that was delivered, information as to the distribution of radiation fluences passing through the patient can be arrived at. Once the sequence of instantaneous fluence patterns have been brought together after a fraction is complete, they can be used in conjunction with anatomical information acquired prior to or during treatment (for example a planning CT scan or intra-fraction MR image(s)) to estimate the three-dimensional dose pattern or dose equivalent that was delivered during that fraction. A significant computational effort is involved, so the calculation is usually done after the fraction is complete, using all of the observed fluence patterns from the fraction, to allow a post-fraction QA check of the dose delivery.

SUMMARY OF THE INVENTION

This process of creating a post-fraction check of the delivered dose is a useful form of quality assurance. However, if there has been a significant error in the treatment planning and/or delivery processes then this QA check will only bring this to light after the incorrect dose has already been delivered. A preferable form of QA would be a real-time check on the instantaneous dose actually being delivered, offering the option to suspend the delivery if an error was evident.

We have realised that the EPID images and/or the individual fluences derived from the EPID images and the delivered beam provide a potential source of data for real-time dosimetry verification provided that a computational route is found that is sufficiently efficient to be performed in the time available.

According to the present invention, an expected dose delivery pattern for the fraction in question is calculated in advance, based on the treatment plan, and used for comparison purposes during the first treatment fraction. All that needs to be calculated during the treatment fraction, therefore, is the incremental increase in the dose that has been delivered based on the observed fluences that are derivable from the EPID data.

The present invention therefore provides a radiotherapy apparatus comprising a source of therapeutic radiation for delivering a dose to a patient, a detector for the therapeutic radiation after attenuation by the patient, and a control unit adapted to:
  i. receive a sequence of dose delivery instructions;
  ii. receive data describing the patient and characterising at least the patient geometry
  iii. using the dose delivery instructions and the patient data, perform a first computational analysis to ascertain an expected dose distribution to be delivered to the patient by performance of an initial subset of the dose delivery instructions in order to produce a first dose distribution;
  iv. subsequent to completion of the first computational analysis, cause the apparatus to perform the dose delivery instructions; and
  v. during the performance of the dose delivery instructions,
     a. acquire the output of the detector;
     b. perform a second computational analysis based on the acquired output in conjunction with the patient data to produce an estimated actual dose distribution, and
     c. compare the estimated actual dose distribution to the expected dose distribution.

The control unit can react to the result of the comparison in a number of ways. A simple alert signal if the comparison shows a significant difference between the subsequent dose distribution and the first dose distribution will enable the operators of the apparatus to intervene and take appropriate action. Alternatively, the discovery of a significant difference could prompt the cessation of the treatment fraction. A difference can be considered significant if it exceeds a predetermined threshold, for example. It may also be possible for the apparatus to compute a corrective action or a damage-mitigating action, especially where the comparison reveals an under-dose, The comparison may be performed as an additive process, wherein the actual dose distribution accumulates and is compared with the expected dose distribution; alternatively, the actual dose distribution may be subtracted from the expected dose distribution. Thus, the comparison may be displayed in a number of different ways to aid a visual display of and/or a practitioner's monitoring of progress of a dose delivery. For example, it may be that monitoring a dose yet to be delivered approach zero is more straightforward to comprehend than monitoring a dose already delivered reach a predetermined level.

In general, steps (0) to (0) will be started on a first calendar day and steps (0) and (0) will take place on a later calendar day. This allows time for the computational analysis of step (0), which may (often) take place overnight.

The computation of step (0) is preferably repeated to derive multiple expected dose distributions corresponding to multiple initial subsets of the dose delivery instructions. An "initial subset" is intended to mean a subset of the entire set of dose delivery instructions which starts with the first instruction and includes a number of subsequent instructions following from the first, up to an instruction which is part-way through the entire set and not including any subsequent instructions. In this way, the multiple expected dose distributions model the progressive development of the delivered dose as the treatment fraction progresses. Ideally, the number of expected dose distributions will be equal to the number of instructions, meaning that the delivered dose after each instruction is modelled and offering the greatest sensitivity to errors in delivery. However, for reasons of computational efficiency this need not be the case. Individual expected dose distributions within a treatment plan need not be identical to each other. For example, if progress of the therapeutic efficacy is monitored and the treatment plan is altered between fractions, or if a treatment plan includes different planned fractions, then individual fractions are likely to result in different expected dose distributions and actual dose distributions.

The source will often include sensors to measure its radiation output, in which case the delivered radiation can be determined by observing a difference between an output beam as measured by the sensors and an attenuated beam as measured by the detector.

The data describing the patient ideally includes at least data defining an external surface of the patient, and can also include data defining at least one of tissue types and tissue densities within the patient. Where it includes just an external surface of the patient, the computational analysis can comprise a back-projection of the stored radiation fluence information through a body that consists of a standard material (such as water) having a shape corresponding to the external surface of the patient, thereby to determine a dose distribution. Such an analysis is straightforward to compute and can therefore be done during the further performance. Where sufficient computing resources are available, the data describing the patient can be in greater detail and the computational analysis can comprise back-projection of the stored radiation fluence information through the defined tissue type information.

This could be done with varying levels of complexity. In one example, 2D images of the patient taken before or during treatment (using various modalities, including Xray, MRI, SPECT or PET etc.) could be used to determine the position and/or density of the various tissue types in relation to the radiation beam prior to or during the treatment fraction. These could then be used in conjunction with the attenuated beam as measured by the detector to determine an estimation of the dose delivered to various tissues within the patient during the course of the fraction, which could be used to determine if the fraction is proceeding according to radiation treatment plan.

In another example, multiple 2D images could be taken of the patient prior to or during treatment in order to generate a 3D volumetric image of the patient. Images taken prior to treatment in this manner could be combined using methods known in the art, for example with a surrogate signal, such as a spirometer or a marker block on the patient in order to account for periodic motion of the patient caused by, for example, breathing, so that 2D images taken during the same phase in the breathing cycle could be combined to create a clearer 3D image of one phase in the patient's breathing cycle. During treatment the same surrogate signal could be used to determine the position of the tissues at the time the attenuated beam image is acquired, in order to more accurately calculate dose deposition within the patient. Alternatively, the radiation beam could be gated so that radiation is only applied to the patient when the patient has reached a particular phase in their breathing cycle, corresponding to that phase for which a 3D image has been reconstructed, in order that the 3D image could be used to determine the dose deposition. In cases where the plurality of 2D images are taken during treatment, such a system could use a surrogate signal or a common clock to match the acquired intra-fraction anatomical images with the corresponding attenuation image, and use these intra-fraction anatomical images to determine the positions of the patient's tissues and in turn to determine the accumulation of dose during the course of the fraction.

In another example, multiple 2D images could be processed to produce multiple 3D images of the patient's target volume, where each 3D image represents the patient's anatomy at one phase in their breathing cycle. These 3D images in turn could be used to model the motion of the patient's internal tissues in 4D. This could be done using methods known in the art, where 3D images generated using multiple 2D images taken during the same phase of the patient's breathing cycle are in turn sequenced so as to create a 40 motion model of the patient's internal anatomical positions (if the images are taken prior to the start of treatment), or real-time 4D cine images where the images of the patient continue to be acquired during the course of the fraction in order to update the 3D images and therefore the 4D cine images. These models or cine images could then be combined with the images of the attenuated beam to determine the deposition of dose in the patient during the course of the fraction on a tissue-by-tissue basis, in order to determine throughout the fraction whether any significant deviations from the planned dose deposition are occurring.

Where no such data exists, such a method could still be applied purely to the attenuated beam as measured by the detector to determine a pattern of radiation exposure accumulated during the fraction, which could be compared to the estimated model.

Patient data such as tissue type information could be obtained by, for example, an atlas-based auto-segmentation software which determines tissue type based on its shape and location in an image compared with a standard, defined reference image, or any suitable alternative software. Tissue type information obtained by such means could be complemented by a lower-resolution method for tracking a surface or boundary of a particular tissue type during the treatment fraction, in order to provide further precision during the performance of the dose delivery instructions. In this way it is only necessary to define the tissue types once, and mark their locations on the image. Thereafter, the boundaries of these tissues could be tracked and used to determine the positions of the tissues in each image. One suitable lower-resolution method for tracking a tissue boundary could be a deformation field analysis; as real-time computational capabilities develop, more precise tissue type tracking could be used with the present invention.

Where the computational ability of the system is limited, an alternative to comparing the dose across the whole detector area may be to make comparisons between sub-regions of the detector. This could either be done by selecting specific groups of pixels on the detector and comparing the dose accumulation in those pixel groups as the fraction progresses, or by selecting a specific sub-region of an identified tissue type (such as tumour, organ, bone, etc.) and monitoring the accumulation of dose in that tissue type sub-region during the progression of the fraction. In either case, the progression of dose accumulation could be compared between fractions to determine if the fraction is progressing as intended, and action taken should it be found that there is significant deviation between dose accumulation patterns during subsequent fractions.

The data describing the patient can be derived from one of a CT scan and an MRI scan of the patient in a generally known manner.

The analysis is preferably carried out on a semi-continuous basis during the fraction. Thus, the control apparatus is preferably arranged to perform the first computational analysis taking into account the acquired information resulting from an initial subset of the steps within the sequence of dose delivery instructions, and perform the second computational analysis during the further performance of the dose delivery instructions and after a corresponding initial subset of the steps within the sequence of dose delivery instructions. A first subset may (for example) comprise steps 1 to 'n' of the sequence of instructions. The control apparatus is ideally arranged to perform multiple pairs of computational analyses after different subsets of the steps within the sequence of dose delivery instructions, such as after a second subset which may comprise steps 1 to 'm' of the sequence of instructions.

Delivered radiation fluence may be measured by the detector. If more information is available, for example if images of patient anatomy are available, then measurements from the detector may be back-projected to estimate a spatial measure of delivered radiation fluence. This back-projected estimate could be compared in the actual dose, as in step v, to the expected dose.

BRIEF DESCRIPTION OF DRAWINGS

An embodiment of the present invention will now be described by way of example, with reference to the accompanying figures in which;

FIG. 1 shows a schematic form of apparatus to which the present application can be applied;

FIG. 2 shows the known comparison process;

DETAILED DESCRIPTION OF THE EMBODIMENTS

Figure 3:
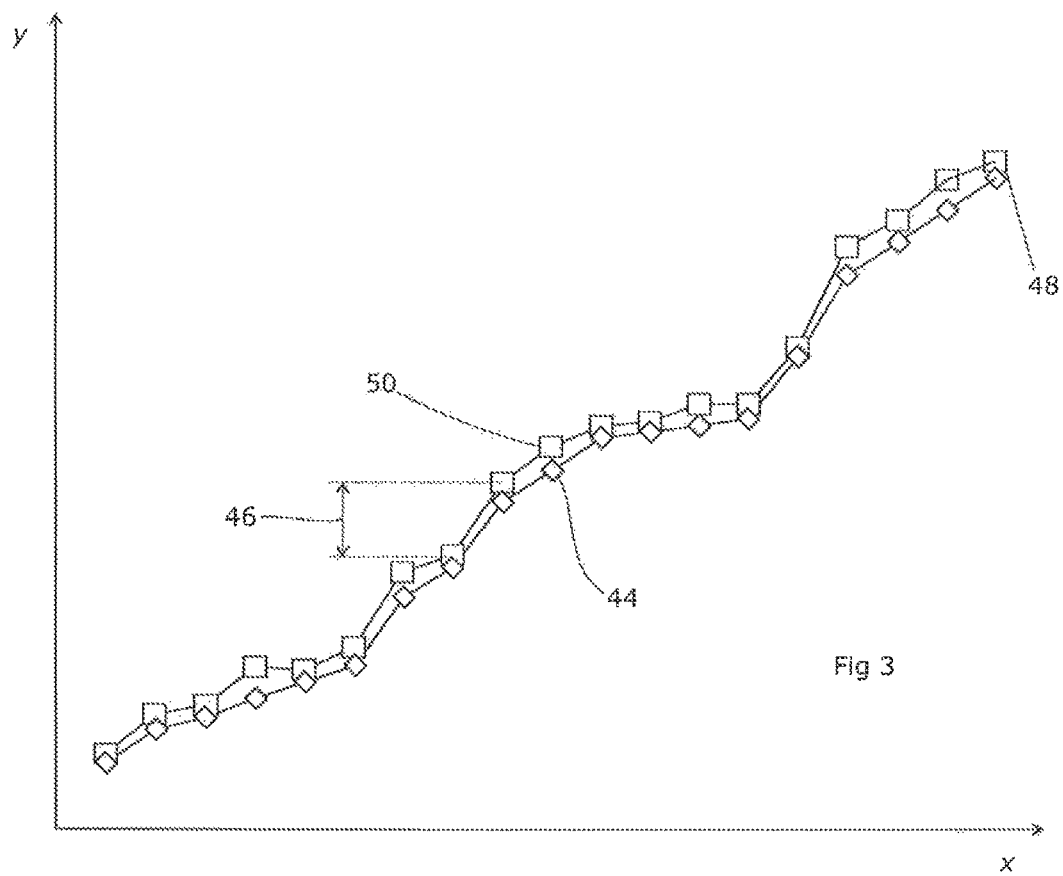
FIG. 3 shows a sample dose development according to the present invention.

FIG. 1 schematically illustrates a radiotherapy apparatus to which the present invention can be applied. A patient 10 including a tumour or other lesion 12 is supported on a patient table 14. This is positionable in a generally known manner which allows the position of the patient 10 to be adjusted in up to 6 axes (three translational, three rotational), thus allowing the tumour 12 to be positioned at a location convenient to the apparatus.

A gantry 16 is provided closely adjacent to the patient table 14, and is rotatable around a horizontal axis 18. As illustrated, the patient table 14 is arranged so that the horizontal axis 18 is generally aligned with the patient's cranio-cordal axis, but in practice the table may be rotated so that the patient is at whatever angle is convenient for the treatment that is intended. Rotation of this type can be useful in moving sensitive structures of the patient out of the field of treatment or into an area of the field that is more easily avoided. An arm (not visible) extends from the gantry 16 and carries a source of therapeutic radiation 20 which emits a beam 22 generally towards the horizontal axis 18. Collimators 24 are provided within the source structure, which are able to shape and direct the beam 22 into a chosen cross-section being a subset of its maximum aperture. One or more sensors 25 are also provided within the source, to measure the radiation output.

As shown in FIG. 1, the source 20 on the gantry 16 is at its uppermost position, thus directing the beam 22 vertically downwardly. As the gantry 16 rotates and carries the source 20 with it, the beam will approach the patient from a range of directions. Assuming that the collimators 24 are used to shape the beam cross-section to the shape of the tumour 12 when viewed along that direction (known as rotational conformal arc therapy) then the effect will be that the tumour 12 remains in the beam at all times whereas surrounding tissue is only briefly irradiated when the gantry 16 is at or passing through one of two particular rotational positions. Thus, this arrangement allows the dose delivered to the tumour to be maintained whilst delivering a significantly lower dose to surrounding tissue.

Other treatment modalities are possible, involving collimator movements that are more complex than the relatively simple rotational conformal arc therapy. In such treatments, the collimation may be adjusted along with the rotation speed of the gantry and the dose rate delivered by the source 20 in order to build up a three-dimensional dose distribution that is optimised around the tumour and the patient's anatomy. Such a dose distribution can ensure a sufficient dose is delivered into the tumour whilst observing maximum permitted doses to other areas, which may vary according to the nature of the tissue at those areas. For example, sensitive areas such as the spinal cord can be protected from radiation doses. Such a dose distribution is delivered by computing a "treatment plan" which consists of the necessary gantry movements, collimator movements, and dose rates which need to take place in order to deliver the distribution. The treatment plan is generally obtained by an iterative computation process which takes into account the dose distribution and the apparatus constraints in a generally known manner to arrive at a treatment plan which is individual to that patient.

The gantry 16 is usually set within a wall 19 so that the relatively bulky mechanisms for supporting the gantry and rotating it accurately can be concealed, allowing a cosmetically acceptable environment for the treatment room.

Also attached to the gantry 16 is an electronic portal imaging device (EPID) 26 in the form of a flat panel detector for the therapeutic radiation, usually using scintillation techniques to derive a digital image of the therapeutic beam. The EPID 26 is positioned on the gantry opposite the source 20 and thus the patient 10 lies between the source 20 and the EPID 26. As a result, the EPID 26 sees the therapeutic beam after attenuation by the patient 10, and thus with knowledge of the nature of the beam that was emitted, and the patient's anatomical information, a measure of the radiation absorbed by the patient can be determined. From the set of such doses obtained throughout the treatment, a three-dimensional representation of the actual dose delivered to the patient, can be computed once the treatment fraction is complete. This computation process takes some time, but is usually available prior to the next treatment fraction. It means that the dose that was actually delivered can be compared to the dose that was planned to be delivered, thus validating the treatment plan and confirming that the treatment fraction was successful. Generally, this is done after each fraction.

Thus, FIG. 2 shows the comparison process in a conventional radiotherapy apparatus. The treatment plan comprises a series of individual sub-doses 28a, 28b, 28c, 28d, 28e, 28f; a specific treatment plan may include more sub-doses or fewer sub-doses as required. Together, these subdoses 28a-28f cumulatively deliver a total dose 30. During the treatment planning stage, this will have been compared to the dose prescribed by the physician and confirmed as being identical or within a set tolerance that is deemed acceptable. The apparatus then delivers the first treatment fraction, delivering sub-doses 32a, 32b, 32c, 32d, 32e, 32f. During this time, the EPID 26 monitors the radiation exiting the patient and records this. After delivery of the fraction, it combines this information with patient-specific anatomical information to determine the sub-doses delivered during the fraction. These sub-doses are summed to create a cumulative dose 34 and a comparison 36 is carried out with the planned dose 30 or the prescribed dose to confirm that any differences are within a set tolerance that is deemed acceptable.

If there are non-trivial differences between the planned or prescribed dose and the dose actually delivered, then an alert is raised to draw the attention of medical staff who can investigate why this has happened. Otherwise, the second fraction can then be delivered in a similar manner. Thus, sub-doses 38a to 38f will be delivered, and monitored throughout by the EPID 26. At the end of the second fraction, a comparison 42 is made between the total dose 40 delivered during that fraction and the planned dose 30 or the prescribed dose, again to confirm that any differences are within a set tolerance that is deemed acceptable. Similar alerts can be raised if a significant difference is observed, or the treatment can continue to a further fraction (if required) in the same way.

Clearly, if there is an error in the delivery of a fraction then this will not be detected until that fraction is complete. Whilst this is obviously better than nothing, it would be useful to be able to detect errors sooner than this. The present invention therefore proposes that an expected dose delivery pattern for the first (and subsequent) fractions be calculated from the treatment plan and used for comparison purposes during the treatment fraction in question. The treatment plan will comprise a series of steps, and the beam shapes that will be delivered by those steps can be modelled. With knowledge of those beam shapes, the dose patterns during delivery of the first fraction can be modelled ideally using the same reconstruction technique as that which is to be used during the treatment fractions. These expected dose distributions can then be used as the basis for comparison with the actual dose distributions reconstructed as the fraction progresses, to compare and determine any variations in the delivery.

To illustrate the concept, imagine a single point dose being calculated per treatment plan step (or with respect to time) as shown in FIG. 3. Along the x axis of FIG. 3 is the progress of the treatment fraction, measured in any convenient scale such as time, or treatment step, or the like. Along the y axis is the dose delivered to the point in question. The diamond-shaped points 44 illustrate the total dose that is expected to be delivered up to that point during that treatment fraction. As can be seen, this increases steadily with each sub-dose 46 until at the end of the treatment the planned total dose 48 has been delivered.

In an actual fraction (such as the first, second, third, fourth etc), the same reconstruction process can be carried out based on the observed EPID fluence measurements to produce a further dose/progress profile, this time illustrated with square points 50. In this case, the square points 50 of the subsequent fraction closely follow the diamond points 44 of the first fraction, indicating that the subsequent fraction is developing in the same manner as the first fraction. This comparison can be made with an acceptable tolerance in mind. Thus, a comparison can be made after each sub-dose 46 of the second and subsequent fractions in order to determine that the fraction is progressing normally. This can be repeated for each point within the tumour, or within the patient, or within a region of interest, depending on the computational load involved and the computational power available. If a significant divergence is detected then an alert can be issued and/or the treatment fraction stopped or suspended. This should (in most cases) result in a lower accidental dose being delivered. It is notable that if the error is in the early part of the treatment and in relation to a location that is to receive a significant dose, then it may be possible to detect a developing error before the prescribed dose 48 has been delivered.

Figure 4:
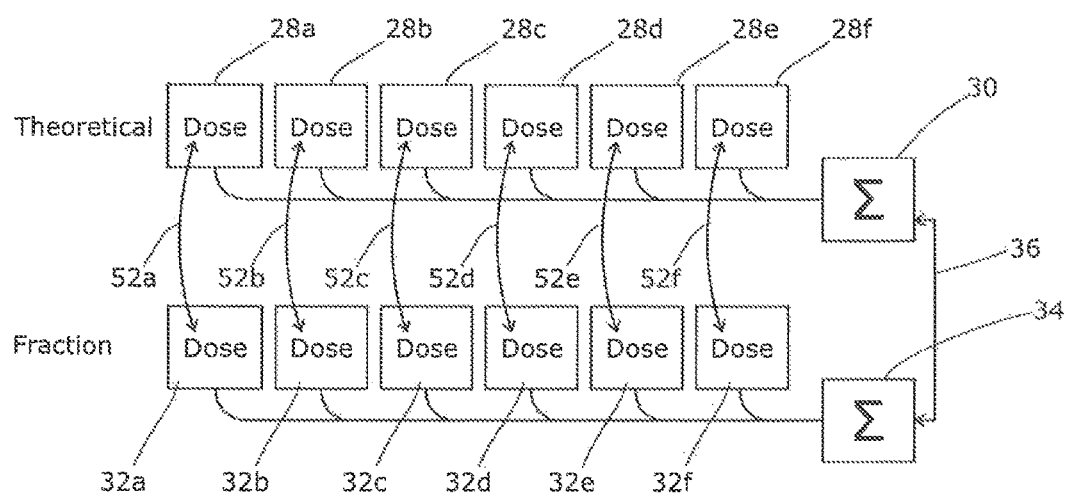
FIG. 4 shows the comparison process according to the present invention.

FIG. 4 shows a version of FIG. 2, showing the additional comparisons provided by the present invention. Thus, in addition to the comparison 36 carried out at the end of the treatment fraction, there are a series of comparisons 52a to 52f between the effects predicted by the planned sub-doses 28x and those produced by the actual sub-doses 32x.

The comparison process can then be repeated for subsequent fractions, each being compared to the dose buildup profiles predicted by computation based on the treatment plan. If the subsequent fractions use the same treatment plan then the same predicted dose buildup profiles can be used.

The dose itself (for each location) is calculated from knowledge of the fluence patterns obtained from the EPIC) and from knowledge of the patient anatomy. The ideal approach is to start from a known shape and internal structure of the patient (i.e. tissue types, tissue densities etc) and reconstruct the observed ray fluences through the patient in order to calculate the dose delivered at each point within the patient, using known techniques. This approach produces the most accurate representation of the dose pattern that was delivered. Alternatively, a less computationally demanding approach is to use only the patient outline and assume that the patient is composed of a uniform standard material, such as water. Without having to take account of internal variations in the patient tissue density, the dose pattern is much easier to compute, allowing it to be done several times within the time required to deliver a treatment fraction. The dose pattern produced in this way is less accurate, but (we have found) is sufficient for the purpose of comparison with other treatment fractions.

Thus, after each sub-dose or after a group of sub-doses, the cumulative dose delivered so far during the fraction can be calculated. These can be compared with the corresponding dose patterns computed using the treatment plan in order to provide a real-time confirmation that the fraction is proceeding as intended.

Thus, by allowing a simpler reconstruction (such as a water model of the patient) and by operating (at any one time) on only a subset of the sub-doses delivered during a fraction (instead of the entire fraction), the present invention reduces the computational load of this type of checking process to one that can be completed in real time as the treatment fraction progresses.

In some systems, the treatment plan for the second or subsequent fractions is adjusted to take account of variations in the size, shape, position of the tumour (etc). Corresponding variations could be made to the recorded data from the first fraction and the patient anatomical information in order to ensure that the comparison remains valid.

It will of course be understood that many variations may be made to the above-described embodiment without departing from the scope of the present invention.

The invention claimed is:

1. A radiotherapy apparatus comprising:
a source of therapeutic radiation for delivering a dose to a patient;
a detector for detecting the therapeutic radiation after attenuation by the patient;
a control unit having a processor configured to execute instructions that, when executed by the processor, cause the control unit to be configured to:
receive a sequence of dose delivery instructions for delivering the dose of radiation to the patient, the sequence comprising a plurality of subsets of the dose delivery instructions;
receive patient data describing a patient geometry;
perform, using a first subset of the dose delivery instructions and the patient data, a first computational analysis to determine a first expected dose distribution to be delivered to the patient, wherein the first computational analysis includes computing radiation fluence information based on an aqueous body having a shape corresponding to the patient geometry;
subsequent to completion of the first computational analysis, cause the apparatus to perform the dose delivery instructions; and
during performance of the dose delivery instructions:
receive a first output from the detector after performance of the first subset of the dose delivery instructions;
perform a second computational analysis based on the received first output and the patient data to determine a first actual dose distribution, wherein the second computational analysis includes computing radiation fluence information based on an aqueous body having a shape corresponding to the patient geometry;
perform a first comparison comparing the first actual dose distribution to the first expected dose distribution;
determine an expected dose accumulation profile for the patient based on a sum of the first expected dose distribution and a second expected dose distribution, wherein the second expected dose distribution is determined by the first computational analysis of a second subset of the dose delivery instructions and the patient data;
determine an actual dose accumulation profile for the patient based on a sum of the first actual dose distribution and a second actual dose distribution, wherein the second actual dose distribution is determined by the second computational analysis of a second output from the detector after performance of a second subset of the dose delivery instructions;
perform a second comparison comparing the actual dose accumulation profile to the expected dose accumulation profile; and
provide an alert signal based on at least one of the first comparison and the second comparison.

2. The radiotherapy apparatus according to claim 1, wherein the control unit is configured to provide the alert signal when the comparison between the first actual dose distribution and the first expected dose distribution exceeds a predetermined threshold.

3. The radiotherapy apparatus according to claim 1, wherein the detector is a portal image detector.

4. The radiotherapy apparatus according to claim 1, wherein the control unit is configured to perform the first computational analysis at a first time corresponding to a first calendar day, and the second computational analysis at a second time corresponding to a second calendar day.

5. The radiotherapy apparatus according to claim 1, wherein the source includes sensors to measure radiation output of the source, and the first actual dose distribution is determined by computing a difference between an output beam measured by the sensors and an attenuated beam measured by the detector.

6. The radiotherapy apparatus according to claim 1, wherein the patient data includes data defining an external surface of the patient.

7. The radiotherapy apparatus according to claim 6, wherein the first computational analysis and the second computational analysis includes using a back-projection algorithm.

8. The radiotherapy apparatus according to claim 1, wherein the patient data includes data defining at least one of tissue types and tissue densities within the patient.

9. The radiotherapy apparatus according to claim 8, wherein the first computational analysis includes back-projection of stored radiation fluence information through the data defining tissue types to determine the first expected dose distribution.

10. The radiotherapy apparatus according to claim 1, wherein the patient data is derived from one of a CT scan and an MRI scan of the patient.

11. The radiotherapy apparatus according to claim 1, wherein the first computational analysis is repeated to determine multiple expected dose distributions corresponding to multiple subsets of the dose delivery instructions.

12. The radiotherapy apparatus according to claim 1, wherein the patient geometry consists of an outline of the patient, and the control unit is configured to perform the second computational analysis based on the detected first output and the patient geometry.

13. A computer-implemented method for delivering a dose of therapeutic radiation from a source to a patient, the method performed by a processor and comprising:
receiving a sequence of dose delivery instructions for delivering the dose of radiation to the patient, the sequence comprising a plurality of subsets of the dose delivery instructions;
receiving patient data describing a patient geometry;
performing a first computational analysis, using a first subset of the dose delivery instructions and the patient data, to determine a first expected dose distribution to be delivered to the patient, wherein the first computational analysis includes computing radiation fluence information based on an aqueous body having a shape corresponding to the patient geometry;

delivering the dose of therapeutic radiation according to the dose delivery instructions after the first computational analysis is complete;

detecting from a detector, after delivery of a first dose according to the first subset of the dose delivery instructions, a first output comprising the therapeutic radiation after attenuation by the patient;

performing a second computational analysis based on the detected therapeutic radiation and the patient data to determine a first actual dose distribution, wherein the second computational analysis includes computing radiation fluence information based on an aqueous body having a shape corresponding to the patient geometry;

performing a first comparison comparing the first actual dose distribution to the first expected dose distribution;

determining an expected dose accumulation profile for the patient based on a sum of the first expected dose distribution and a second expected dose distribution, wherein the second expected dose distribution is determined by the first computational analysis of a second subset of the dose delivery instructions and the patient data;

determining an actual dose accumulation profile for the patient based on a sum of the first actual dose distribution and a second actual dose distribution, wherein the second actual dose distribution is determined by the second computational analysis of a second output from the detector after performance of a second subset of the dose delivery instructions;

performing a second comparison comparing the actual dose accumulation profile to the expected dose accumulation profile; and providing an alert signal based on at least one of the first comparison and the second comparison.

14. The computer-implemented method according to claim 13, wherein the source includes sensors to measure radiation output of the source, and the first actual dose distribution is determined by computing a difference between an output beam measured by the sensors and an attenuated beam measured by the detector.

15. The computer-implemented method according to claim 13, wherein performing the first computational analysis includes performing the first computational analysis at a first time corresponding to a first calendar day and performing the second computational analysis includes performing the second computational analysis at a second time corresponding to a second calendar day.

16. The computer-implemented method according to claim 13, wherein the first computational analysis is repeated to determine multiple expected dose distributions corresponding to multiple subsets of the dose delivery instructions.

17. The computer-implemented method according to claim 13, wherein the patient geometry consists of an outline of the patient, and the processor performs the second computational analysis based on the detected first output and the patient geometry.

* * * * *